(12) United States Patent
Castro

(10) Patent No.: US 9,402,734 B2
(45) Date of Patent: Aug. 2, 2016

(54) SPACER FOR SPINAL IMPLANT

(71) Applicant: IGIP, LLC, Louisville, KY (US)

(72) Inventor: Frank Castro, Louisville, KY (US)

(73) Assignee: IGIP, LLC, Louisville, KY (US)

( * ) Notice: Subject to any disclaimer, the term of this patent is extended or adjusted under 35 U.S.C. 154(b) by 0 days.

(21) Appl. No.: 14/960,394

(22) Filed: Dec. 6, 2015

(65) Prior Publication Data

US 2016/0095711 A1    Apr. 7, 2016

Related U.S. Application Data

(60) Continuation-in-part of application No. 14/457,323, filed on Aug. 12, 2014, now Pat. No. 9,259,323, which is a division of application No. 13/199,418, filed on Aug. 30, 2011, now Pat. No. 8,986,383, which is a continuation-in-part of application No. 12/804,867, filed on Jul. 30, 2010, now Pat. No. 8,673,006.

(51) Int. Cl.
*A61F 2/44*    (2006.01)
*A61F 2/30*    (2006.01)

(52) U.S. Cl.
CPC ............. *A61F 2/442* (2013.01); *A61F 2/30744* (2013.01); *A61F 2/44* (2013.01); *A61F 2/447* (2013.01); *A61F 2002/30032* (2013.01); *A61F 2002/30062* (2013.01); *A61F 2002/30158* (2013.01); *A61F 2002/30271* (2013.01); *A61F 2002/30354* (2013.01); *A61F 2002/30481* (2013.01); *A61F 2002/30578* (2013.01); *A61F 2002/30604* (2013.01); *A61F 2210/0004* (2013.01); *A61F 2220/0025* (2013.01); *A61F 2220/0033* (2013.01); *A61F 2230/0026* (2013.01); *A61F 2230/0082* (2013.01); *A61F 2250/003* (2013.01); *A61F 2310/00017* (2013.01); *A61F 2310/00023* (2013.01)

(58) Field of Classification Search
CPC .................................. A61F 2/447; A61F 2/44
USPC ............................................. 623/17.11–17.16
See application file for complete search history.

(56) References Cited

U.S. PATENT DOCUMENTS

| 5,147,402 | A | | 9/1992 | Bohler et al. |
| 5,192,327 | A | | 3/1993 | Brantigan |
| 5,425,772 | A | | 6/1995 | Brantigan |
| 5,458,638 | A | | 10/1995 | Kuslich et al. |
| 5,558,674 | A | * | 9/1996 | Heggeness ......... A61B 17/1757 606/264 |
| 5,609,635 | A | | 3/1997 | Michelson |

(Continued)

FOREIGN PATENT DOCUMENTS

GB    2364643    2/2002

OTHER PUBLICATIONS

Barack, R. L., Revision Total Hip Anthroplasty: The Femoral Component. J. Am Acad Orthop Surg 1995; 3(2); 79-85. USA.

(Continued)

*Primary Examiner* — Ellen C Hammond
*Assistant Examiner* — Stuart S Bray
(74) *Attorney, Agent, or Firm* — Kenneth F. Pearce

(57) ABSTRACT

The present invention is a spinal implant that can be inserted into a surgically created cavity of one or more regions of the mammalian spine. Among other things, the biocompatible implant and end cap or biocompatible implant, end cap and spacer combinations can assist with the restoration of the normal anatomic spinal alignment and spinal stability.

10 Claims, 7 Drawing Sheets

(56) References Cited

U.S. PATENT DOCUMENTS

| | | | |
|---|---|---|---|
| 5,766,252 A | 6/1998 | Henry et al. | |
| 5,888,228 A * | 3/1999 | Knothe | A61F 2/446 623/17.16 |
| 5,968,098 A * | 10/1999 | Winslow | A61B 17/025 606/248 |
| 5,980,522 A * | 11/1999 | Koros | A61F 2/4455 606/60 |
| 6,066,175 A | 5/2000 | Henderson et al. | |
| 6,080,193 A | 6/2000 | Hochshuler et al. | |
| 6,090,143 A | 7/2000 | Meriwether et al. | |
| 6,117,174 A | 9/2000 | Nolan | |
| 6,159,244 A | 12/2000 | Suddaby | |
| 6,159,245 A | 12/2000 | Meriwether et al. | |
| 6,231,610 B1 | 5/2001 | Geisler | |
| 6,287,343 B1 | 9/2001 | Kuslich et al. | |
| 6,302,914 B1 | 10/2001 | Michelson | |
| 6,395,030 B1 * | 5/2002 | Songer | A61B 17/70 623/17.11 |
| 6,395,035 B2 | 5/2002 | Bresina et al. | |
| 6,409,766 B1 | 6/2002 | Brett | |
| 6,432,107 B1 | 8/2002 | Ferree | |
| 6,491,724 B1 | 12/2002 | Ferree | |
| 6,537,320 B1 | 3/2003 | Michelson | |
| 6,562,074 B2 * | 5/2003 | Gerbec | A61F 2/4455 623/17.15 |
| 6,569,201 B2 | 5/2003 | Moumene et al. | |
| 6,576,016 B1 | 6/2003 | Hochshuler et al. | |
| 6,582,432 B1 | 6/2003 | Michelson | |
| 6,613,091 B1 * | 9/2003 | Zdeblick | A61B 17/1671 623/17.11 |
| 6,641,614 B1 * | 11/2003 | Wagner | A61F 2/4455 623/17.15 |
| 6,648,917 B2 | 11/2003 | Gerbec et al. | |
| 6,660,038 B2 | 12/2003 | Boyer et al. | |
| 6,712,825 B2 | 3/2004 | Aebi et al. | |
| 6,712,852 B1 | 3/2004 | Chung et al. | |
| 6,746,484 B1 | 6/2004 | Liu et al. | |
| 6,761,738 B1 | 7/2004 | Boyd | |
| 6,767,367 B1 | 7/2004 | Michelson | |
| 6,776,798 B2 * | 8/2004 | Camino | A61F 2/44 623/17.16 |
| 6,805,714 B2 | 10/2004 | Sutcliffe | |
| 6,808,538 B2 * | 10/2004 | Paponneau | A61F 2/44 623/17.16 |
| 6,837,905 B1 | 1/2005 | Liberman | |
| 6,852,129 B2 | 2/2005 | Gerbec et al. | |
| 6,863,673 B2 | 3/2005 | Gerbec et al. | |
| 6,926,737 B2 * | 8/2005 | Jackson | A61F 2/446 623/17.11 |
| 6,929,662 B1 | 8/2005 | Messerli et al. | |
| 6,942,697 B2 | 9/2005 | Lange et al. | |
| 6,997,953 B2 | 2/2006 | Chung et al. | |
| D524,942 S | 7/2006 | Felix | |
| 7,166,110 B2 | 1/2007 | Yundt | |
| 7,182,782 B2 * | 2/2007 | Kirschman | A61B 17/7059 606/279 |
| 7,232,463 B2 | 6/2007 | Falahee | |
| 7,594,931 B2 | 9/2009 | Louis et al. | |
| 7,621,953 B2 | 11/2009 | Braddock, Jr. et al. | |
| 8,016,887 B1 * | 9/2011 | Castro | A61F 2/44 623/17.11 |
| 8,491,653 B2 | 7/2013 | Zucherman | |
| 8,986,383 B2 | 3/2015 | Castro | |
| 9,084,684 B2 * | 7/2015 | Castro | A61F 2/446 |
| 2002/0099443 A1 | 7/2002 | Messerli et al. | |
| 2002/0138142 A1 * | 9/2002 | Castro | A61F 2/4465 623/17.11 |
| 2003/0125739 A1 | 7/2003 | Bagga et al. | |
| 2003/0199980 A1 * | 10/2003 | Siedler | A61F 2/44 623/17.11 |
| 2004/0064184 A1 | 4/2004 | Chung et al. | |
| 2004/0073314 A1 * | 4/2004 | White | A61F 2/4455 623/17.15 |
| 2004/0126407 A1 | 7/2004 | Falahee | |
| 2004/0153155 A1 | 8/2004 | Chung et al. | |
| 2004/0153160 A1 * | 8/2004 | Carrasco | A61F 2/4611 623/17.15 |
| 2004/0176842 A1 | 9/2004 | Middleton | |
| 2004/0199254 A1 | 10/2004 | Louis | |
| 2004/0204714 A1 | 10/2004 | Liu et al. | |
| 2004/0225360 A1 * | 11/2004 | Malone | A61B 17/7064 623/17.11 |
| 2005/0071006 A1 | 3/2005 | Kirschman | |
| 2005/0071008 A1 * | 3/2005 | Kirschman | A61B 17/7059 623/17.11 |
| 2005/0149192 A1 * | 7/2005 | Zucherman | A61B 17/1671 623/17.11 |
| 2005/0159813 A1 | 7/2005 | Molz, IV et al. | |
| 2006/0058879 A1 * | 3/2006 | Metz-Stavenhagen | A61F 2/44 623/17.15 |
| 2006/0178752 A1 | 8/2006 | Yaccarino, III et al. | |
| 2006/0235406 A1 * | 10/2006 | Silverman | A61B 17/80 606/71 |
| 2006/0287725 A1 | 12/2006 | Miller | |
| 2007/0016295 A1 | 1/2007 | Boyd | |
| 2007/0123987 A1 * | 5/2007 | Bernstein | A61F 2/44 623/17.11 |
| 2007/0129805 A1 * | 6/2007 | Braddock | A61F 2/30744 623/17.11 |
| 2007/0250167 A1 | 10/2007 | Bray et al. | |
| 2007/0255409 A1 * | 11/2007 | Dickson | A61F 2/30744 623/17.11 |
| 2007/0255413 A1 * | 11/2007 | Edie | A61F 2/44 623/17.16 |
| 2008/0015694 A1 | 1/2008 | Tribus | |
| 2008/0021476 A1 * | 1/2008 | Kirschman | A61B 17/7059 606/288 |
| 2008/0114454 A1 * | 5/2008 | Peterman | A61F 2/44 623/17.16 |
| 2008/0132901 A1 * | 6/2008 | Recoules-Arche | A61F 2/4465 606/99 |
| 2008/0275506 A1 * | 11/2008 | Baynham | A61F 2/447 606/261 |
| 2009/0036985 A1 * | 2/2009 | Whiting | A61F 2/30744 623/17.11 |
| 2009/0138083 A1 * | 5/2009 | Biyani | A61F 2/44 623/17.11 |
| 2009/0234364 A1 * | 9/2009 | Crook | A61F 2/4465 606/99 |
| 2010/0004752 A1 | 1/2010 | White et al. | |
| 2010/0305701 A1 * | 12/2010 | Castro | A61F 2/447 623/17.11 |
| 2012/0004730 A1 * | 1/2012 | Castro | A61F 2/30744 623/17.16 |

OTHER PUBLICATIONS

Castro, F. P., Jr. Stingers, Cervical Cord Neurapraxia, and Stenosis. Clin Sport Med 2003; 22:483-492. USA.

Majd, M.E., Vadhva, M., Holt, R.T. Anterior Cervical Reconstruction Using Titanium Cages With Anterior Plating. Spine 1999; 24(15):1604-1610. USA.

Park, J.B., Cho, Y.S., Riew, K.D. Development of Adjacent-Level Ossification in Patient with an Anterior Cervical Plate. J. Bone Surg. 2005; 87-A: 558-563. USA.

* cited by examiner

SPACER FOR SPINAL IMPLANT

This application is a Continuation-in-Part of application for Letters Patent Ser. No. 14/457,323 entitled—End Cap and Connector for a Spinal Implant—filed Aug. 12, 2014 that was a Division of application for Letters Patent Ser. No. 13/199,418 entitled—End Cap and Connector for Spinal Implant—filed Aug. 30, 2011, now U.S. Pat. No. 8,986,383 issued Mar. 24, 2015, that was a Continuation-in-Part of pending application for Letters Patent Ser. No. 12/804,867 entitled—Spinal Implant—filed on Jul. 30, 2010, now U.S. Pat. No. 8,673,006 issued Mar. 18, 2014.

BACKGROUND OF THE INVENTION

A. Field of the Invention

Among other things, the present invention is related to a spacer for surgical implant or a combination of a first spinal device, a second spinal device and a spacer. Inclusion of the spacer between the first spinal device and the second spinal device allows the spinal column to be distracted a greater length than the length of the two spinal devices.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

U.S. Pat. No. 6,863,673—Gerbec, et al., U.S. Pat. No. 6,852,129—Gerbec, et al., U.S. Pat. No. 6,562,074—Gerbec, et al. and U.S. Pat. No. 6,648,917—Gerbec, et al. disclose adjustable bone fusion implants and methods. U.S. Pat. No. 6,863,673—Gerbec, et al., U.S. Pat. No. 6,852,129—Gerbec, et al., U.S. Pat. No. 6,562,074—Gerbec, et al. claim a chain of priority to U.S. Pat. No. 6,648,917—Gerbec, et al. U.S. Pat. No. 6,863,673—Gerbec, et al. is illustrative of the disclosures of each of the Gerbec, et al. Patents.

By way of example, U.S. Pat. No. 6,863,673—Gerbec, et al., in part reads, "As depicted in FIG. 5A, reinforcing member 16 is in the form of a substantially U-shaped clip. Specifically, reinforcing member 16 comprises a substantially U-shaped cantilever beam 124 which includes an elongated base 126 having supports 128 and 130 upstanding from each opposing end thereof. Forwardly projecting from the top end of support 128 and 130 is an elongated flexible arm 132 and 134, respectively. Each arm 132 and 134 terminates at a free end 136 having an inwardly facing latching barb 138 formed thereat. Each latching barb 138 has a sloped forward surface 140 and an orthogonally disposed inside surface 142. Reinforcing member 16 has a width extending between the outside of opposing arms 132 and 134 that is substantially the same as the maximum width of cap 12 and base 14.

Once cap 12 is selectively elevated relative to base 14, a gap 146 is formed between cap plate 18 and each biasing rail 111 and 112. Reinforcing member 16 is configured such that each arm 132 and 134 can be slidably received within a corresponding gap 146 on each side of housing 11. Sloping surface 140 on each latching barb 138 biases against support members 48-51 and/or the threads thereon causing arms 132, 134 and/or cantilever beam 124 to outwardly bend, thereby enabling latching barbs 138 to pass over support members 48-51. As latching barbs 138 pass over support members 50 and 51, the resilient flexing of arms 132, 134 causes latching barbs 138 to inwardly bias and catch behind support members 50 and 51. The engagement of flat inside surface 142 of each latching barb 138 against the flat side of support members 50 and 51 prevents reinforcing member 116 from unintentionally disconnecting with housing 15. However, in one embodiment arms 132 and 134 are sufficiently flexible that reinforcing member 16 can be removed from housing 11 by simply pulling back on cantilever beam 124. In this regard, reinforcing member 16 is removably positioned. In the assembled configuration shown in FIG. 5B, reinforcing member 16 is positioned between cap plate 18 and base plate 70. More specifically, any compressive force 122 applied to the assembled fusion implant 10 causes arms 132 and 134 of reinforcing member 16 to be compressed between cap plate 18 and biasing rails 111 and 112. As a result, the compressive load is carried primarily through reinforcing member 16 as opposed to through interlocking teeth 60 and 100. In such configuration, some embodiments of fusion implant 10 are capable of withstanding over 2,000 pounds of compressive force without failure or permanent deformation.

As previously discussed, gap size 146 can be selectively incrementally increased by adjusting which teeth 60 and 100 are meshed together. In one embodiment, a discrete reinforcing member is provided for each gap size 146. For example, depicted in FIGS. 5A and 5B, reinforcing member 16 is configured to be received within gap 146 so as to produce a relatively close tolerance. Depicted in FIGS. 6A and 6B, a gap 150 is formed between cap plate 18 and biasing rails 111 and 112. Gap 150 has a height greater than the height of gap 146. For example, gap 146 may correspond to a single tooth spacing while gap 150 corresponds to a spacing of two or more teeth. As such, a reinforcing member 152 is provided. Although reinforcing member 152 has the same structural elements as reinforcing member 16, arms 132 and 134 thereof have an increased height so as to selectively receive within gap 150 under a relatively close tolerance. It is appreciated that a plurality of reinforcing members can be provided with each reinforcing member being configured to fit a different sized gap formed between cap plate 18 and biasing rails 111 and 112. In an alternative embodiment, it is also appreciated that instead of using a larger reinforcing member, a plurality of smaller reinforcing members can be used to fill a single gap. This configuration minimizes the requirement of having to maintain a number of different sizes of reinforcing members.

As depicted in FIGS. 5B and 6B, the purpose of using U-shaped cantilever beam 124 is that beam 124 only covers a portion of access mouth 116. An opening 154 remains that provides communication with compartment 8. As discussed below, opening 154 can be used for feeding bone graft into compartment 8.

Depicted in FIG. 6C is an alternative embodiment of a reinforcing member 197. Reinforcing member 197 comprises a face plate 198 having arms 132 and 134, as previously discussed, projecting therefrom. In one embodiment of the present invention, means are provided for removably connecting an insertion tool to reinforcing member 197. By way of example and not by limitation, a threaded aperture 199 extends through face plate 198. As will be discussed below in greater detail, threaded aperture 199 enable a tubular insertion tool to be threadedly engaged to aperture 199. The bone graft can then be passed down through the tubular insertion tool and into compartment 8. Examples of alternative embodiments of the means for removably connecting an insertion tool to reinforcing member 197 include the same alternatives as previously discussed with regard to the means for removably connecting an insertion tool to attachment wall 68. Each of the components of fusion implant 10 is made from a medical grade biocompatible material. In one embodiment, the components are molded from a carbon fiber reinforced polyetheretherketone polymer. In alternative embodiments, the components can be molded, cut, machined, or otherwise formed from medical grade biocompatible metals, polymers, ceramics, or other materials that have adequate strength. It is also appreciated that different components can be made from different materials. For example, the reinforcing member can be made of metal while the remainder is formed from a plastic. Although fusion implant 10 can be used for fusing together a variety of different bone matter together, illustrated below for purposes of example is one method of using fusion implant 10 for fusing together adjacent vertebrae in a spine. Specifically, depicted in FIG. 7A is a pair of adjacent vertebrae 156 and 158. A posterior opening has been made through the back of the person so as to expose vertebrae 156 and 158. A disk or portion of a disk has been removed from between vertebrae 156 and 158 so that a gap 160 is formed therebetween. Because of the select vertebrae, gap 160 is wedged shaped having a wider portion that faces anteriorly towards the front of a patient and is narrower posteriorly towards the back of the patient.

To optimize fusing of vertebrae 156 and 158 while minimizing post-operative complications, a wedged shaped fusion implant having a size substantially corresponding to gap 160 should be inserted within gap 160. Because gap 160 narrows posteriorly, conventional procedures have required that if a wedged shaped implant was to be inserted within gap 160, it would have to be inserted anteriorly through the front of the patient. Inserting through the front of the patient, however, significantly complicates the procedures in that it requires the surgeon to navigate around a number organs and blood vessels. The other conventional option was to insert a flat, i.e., non-wedged shaped, fusion implant posteriorly into gap 160. Since the fusion implant was flat, however, it would not properly fit gap 160, thereby raising the specter of potential post-operative complications. As discussed below, the present invention enables the posterior insertion of a wedged shaped fusion implant into gap 160, thereby optimizing the benefits. Of course, in alternative uses the applicable gap may not be wedged shaped. The fusion implant thus need not be wedged shaped but can be shaped according to its intended use."

Among other things, it does not appear that the Gerbec invention practices, "A spinal implant inserted about a surgically created cavity proximate to one or more vertebrae; said spinal implant comprising: a) a biocompatible cage comprising: i) a length having a central longitudinal axis and a plurality of sides, wherein at least some of said sides comprise a plurality of openings surrounding a channel; said openings capable of exposing osteogenic substances to said surgically created cavity; and ii) a first end perimeter comprising an open entry into said channel; b) an end cap comprising: i) a border facing said biocompatible cage; ii) a plate extending in a lengthwise direction, parallel said central longitudinal axis, away from said border and comprising at least one opening capable of receiving a fastener; and iii) a pair of opposed docking slides extending from said border toward said biocompatible cage; said docking slides adapted to engage inward sides of said biocompatible cage, wherein said docking slides' surfaces engaging said inward sides of said biocompatible cage are without surface areas adapted for impeding removal of said docking slides from said biocompatible cage; and c) a spacer adapted for allowing adjustment of length of said spinal implant and sandwiched between said biocompatible cage and said end cap; said spacer comprising: i) a first leg extending toward the inward side of said spinal implant; ii) a second leg opposed from said first leg and extending toward the inward side of said spinal implant; and iii) an anterior section anterior to said plate; said anterior section sharing a margin with outward ends of said first and said second legs and extending in a lengthwise direction parallel said central longitudinal axis."

Among other things, it does not appear that the Gerbec invention practices, "A combination comprising a spacer positioned between a surgically implanted first spinal device and a surgically implanted second spinal device, wherein said first and said second spinal devices include a common longitudinal axis; said spacer comprising: a) a first leg sandwiched between said first and said second spinal devices, wherein said first leg comprises a first side comprising apertures adapted to engage some of a plurality of spikes extending, parallel said longitudinal axis, from one of said spinal devices; b) a second leg sandwiched between said first and said second spinal devices, wherein said second leg comprises a first side comprising apertures adapted to engage some of said spikes extending, parallel said longitudinal axis, from said one of said spinal devices; and c) an anterior section anterior to said first and said second spinal devices and connected with an outward end of said first leg and an outward end of said second leg."

U.S. Pat. No. 6,641,614—Wagner et al. discloses a multi-variable-height fusion device. Wagner, in part, reads, "An alternate embodiment of an interbody fusion device is depicted in FIGS. 25-27. FIG. 25 is a perspective view of the fusion device in a lowered position. FIG. 26 is a perspective view of the fusion device in a raised position. FIG. 27 is an exploded view of the fusion device. Fusion device 200 includes a pair of engaging plates 202 and 204 for engaging adjacent vertebrae. Engaging plates 202 and 204 are preferably separated by bracket assembly 206. Engaging plates 202 and 204 and bracket assembly 206 may be formed of titanium, stainless steel, polymer, ceramic, composite material, or any other biocompatible material. For purposes of this description, "biocompatible material" is material not rejected by the body and/or not causing infection following implantation.

As depicted in FIG. 27, engaging plates 202 and 204 may contain a plurality of protrusions 216 from outer surfaces 203 for enhancing an engagement between the vertebrae and the engaging plates. In this manner, subsidence of the vertebrae may be substantially prevented as previously described. Outer surfaces 203 are preferably substantially planar to provide a large contact area between the engaging plates and the vertebrae; alternately, outer surfaces 203 may be non-planar. Protrusions 216 may extend into the vertebrae to prevent the fusion device from moving out of the disc space. Engaging plates 202 and 204 may include a plurality of openings 218 to allow bone development and growth through the engaging plates and between fusion device 200 and the neighboring vertebrae. In an embodiment, openings 218 have a combined area that is greater than about 50% of the total area of outer surfaces 203 (including the area of openings 218). More preferably, openings 218 have a total area between 60% and 80% of the total area of outer surfaces 203. More preferably still, openings 218 have a total area of 70% or more of the total area of outer surfaces 203."

Among other things, it does not appear that the Wagner invention practices, "A spinal implant inserted about a surgically created cavity proximate to one or more vertebrae; said spinal implant comprising: a) a biocompatible cage comprising: i) a length having a central longitudinal axis and a plurality of sides, wherein at least some of said sides comprise a plurality of openings surrounding a channel; said openings capable of exposing osteogenic substances to said surgically created cavity; and ii) a first end perimeter comprising an open entry into said channel; b) an end cap comprising: i) a border facing said biocompatible cage; ii) a plate extending in a lengthwise direction, parallel said central longitudinal axis, away from said border and comprising at least one extending from said border toward said biocompatible cage; said docking slides adapted to engage inward sides of said biocompatible cage, wherein said docking slides' surfaces engaging said inward sides of said biocompatible cage are without surface areas adapted for impeding removal of said docking slides from said biocompatible cage; and c) a spacer adapted for allowing adjustment of length of said spinal implant and sandwiched between said biocompatible cage and said end cap; said spacer comprising: i) a first leg extending toward the inward side of said spinal implant; ii) a second leg opposed from said first leg and extending toward the inward side of said spinal implant; and iii) an anterior section anterior to said plate; said anterior section sharing a margin with outward ends of said first and said second legs and extending in a lengthwise direction parallel said central longitudinal axis."

Among other things, it does not appear that the Wagner invention practices, "A combination comprising a spacer positioned between a surgically implanted first spinal device and a surgically implanted second spinal device, wherein said first and said second spinal devices include a common longitudinal axis; said spacer comprising: a) a first leg sandwiched between said first and said second spinal devices, wherein said first leg comprises a first side comprising apertures adapted to engage some of a plurality of spikes extending, parallel said longitudinal axis, from one of said spinal devices; b) a second leg sandwiched between said first and said second spinal devices, wherein said second leg comprises a first side comprising apertures adapted to engage some of said spikes extending, parallel said longitudinal axis, from said one of said spinal devices; and c) an anterior section anterior to said first and said second spinal devices and connected with an outward end of said first leg and an outward end of said second leg."

SUMMARY OF THE INVENTION

Unlike traditional spinal implants, the present invention provides a biocompatible cage that assists the surgical team in not impinging the spinal cord with the implant. Post operative and prior to complete arthrodesis, the combination of first and second spinal devices and the current spacer inhibit extrusion of the cage against the spinal cord. Utilization of an end cap with the biocompatible implant supplements stabilization of the biocompatible implant. And inclusion of a spacer positioned between the first spinal device and the second spinal device allows the spinal column to be distracted to a greater distance than the length of the cage and the end cap of the biocompatible implant.

An aspect of the present invention is to provide a spacer utilizable with a first spinal device and a second spinal device.

Still another aspect of the present invention is to provide a generally wedge-like cage.

It is still another aspect of the present invention to provide an implant having select embodiments that can be implanted through the patient's frontal or rearward side.

Yet still another aspect of the present invention is to provide a cage that can be severed across a first cross-section or severed across a first cross-section and a second cross-section to create a custom fitted implant for the surgically created cavity.

Still another aspect of the present invention is to provide a biocompatible cage including brakes.

Yet another aspect of the present invention is to provide an end cap attachable to vertebra for assisting with the stabilization of the spinal implant.

It is still another aspect of the present invention to provide a spacer capable of extending the length of the spinal implant.

Still another aspect of the present invention is to provide a spinal implant or a combination of spinal devices capable of enhancing lordosis.

A preferred embodiment of the current invention can be described as a spinal implant inserted about a surgically created cavity proximate to one or more vertebrae; said spinal implant comprising: a) a biocompatible cage comprising: i) a length having a central longitudinal axis and a plurality of sides, wherein at least some of said sides comprise a plurality of openings surrounding a channel; said openings capable of exposing osteogenic substances to said surgically created cavity; and ii) a first end perimeter comprising an open entry into said channel; b) an end cap comprising: i) a border facing said biocompatible cage; ii) a plate extending in a lengthwise direction, parallel said central longitudinal axis, away from said border and comprising at least one opening capable of receiving a fastener; and iii) a pair of opposed docking slides extending from said border toward said biocompatible cage; said docking slides adapted to engage inward sides of said biocompatible cage; and c) a spacer adapted for allowing adjustment of length of said spinal implant and sandwiched between said biocompatible cage and said end cap; said spacer comprising: i) a first leg extending toward the inward side of said spinal implant; ii) a second leg opposed from said first leg and extending toward the inward of said spinal implant; iii) a first ridge positioned on said central longitudinal axis facing side of said first leg and a corresponding second ridge positioned on an said central longitudinal axis facing side of said second leg; and iv) an anterior section anterior to said plate; said anterior section sharing a margin with outward ends of said first and said second legs and extending in a lengthwise direction parallel said central longitudinal axis, wherein said docking slides engage a catch created by an arrangement of said first ridge, said second ridge and said margin.

Another preferred embodiment of the current invention can be described as a spinal implant inserted about a surgically created cavity proximate to one or more vertebrae; said spinal implant comprising: a) a biocompatible cage comprising: i) a length having a central longitudinal axis and a plurality of sides, wherein at least some of said sides comprise a plurality of openings surrounding a channel; said openings capable of exposing osteogenic substances to said surgically created cavity; and ii) a first end perimeter comprising an open entry into said channel; b) an end cap comprising: i)a border facing said biocompatible cage; ii) a plate extending in a lengthwise direction, parallel said central longitudinal axis, away from said border and comprising at least one opening capable of receiving a fastener; and iii) a pair of opposed docking slides extending from said border toward said biocompatible cage; said docking slides adapted to engage inward sides of said biocompatible cage, wherein said docking slides' surfaces engaging said inward sides of said biocompatible cage are without surface areas adapted for impeding removal of said docking slides from said biocompatible cage; and c) a spacer adapted for allowing adjustment of length of said spinal implant and sandwiched between said biocompatible cage and said end cap; said spacer comprising: i) a first leg extending toward the inward side of said spinal implant; ii) a second leg opposed from said first leg and extending toward the inward side of said spinal implant; and iii) an anterior section anterior to said plate; said anterior section sharing a margin with outward ends of said first and said second legs and extending in a lengthwise direction parallel said central longitudinal axis.

Still another preferred embodiment of the current invention can be described as a combination comprising a spacer positioned between a surgically implanted first spinal device and a surgically implanted second spinal device, wherein said first and said second spinal devices include a common longitudinal axis; said spacer comprising: a) a first leg sandwiched between said first and said second spinal devices, wherein said first leg comprises a first side comprising apertures adapted to engage some of a plurality of spikes extending, parallel said longitudinal axis, from one of said spinal devices; b) a second leg sandwiched between said first and said second spinal devices, wherein said second leg comprises a first side comprising apertures adapted to engage some of said spikes extending, parallel said longitudinal axis, from said one of said spinal devices; and c) an anterior section anterior to said first and said second spinal devices and connected with an outward end of said first leg and an outward end of said second leg.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

DESCRIPTION OF THE PREFERRED EMBODIMENTS

Figure 1:
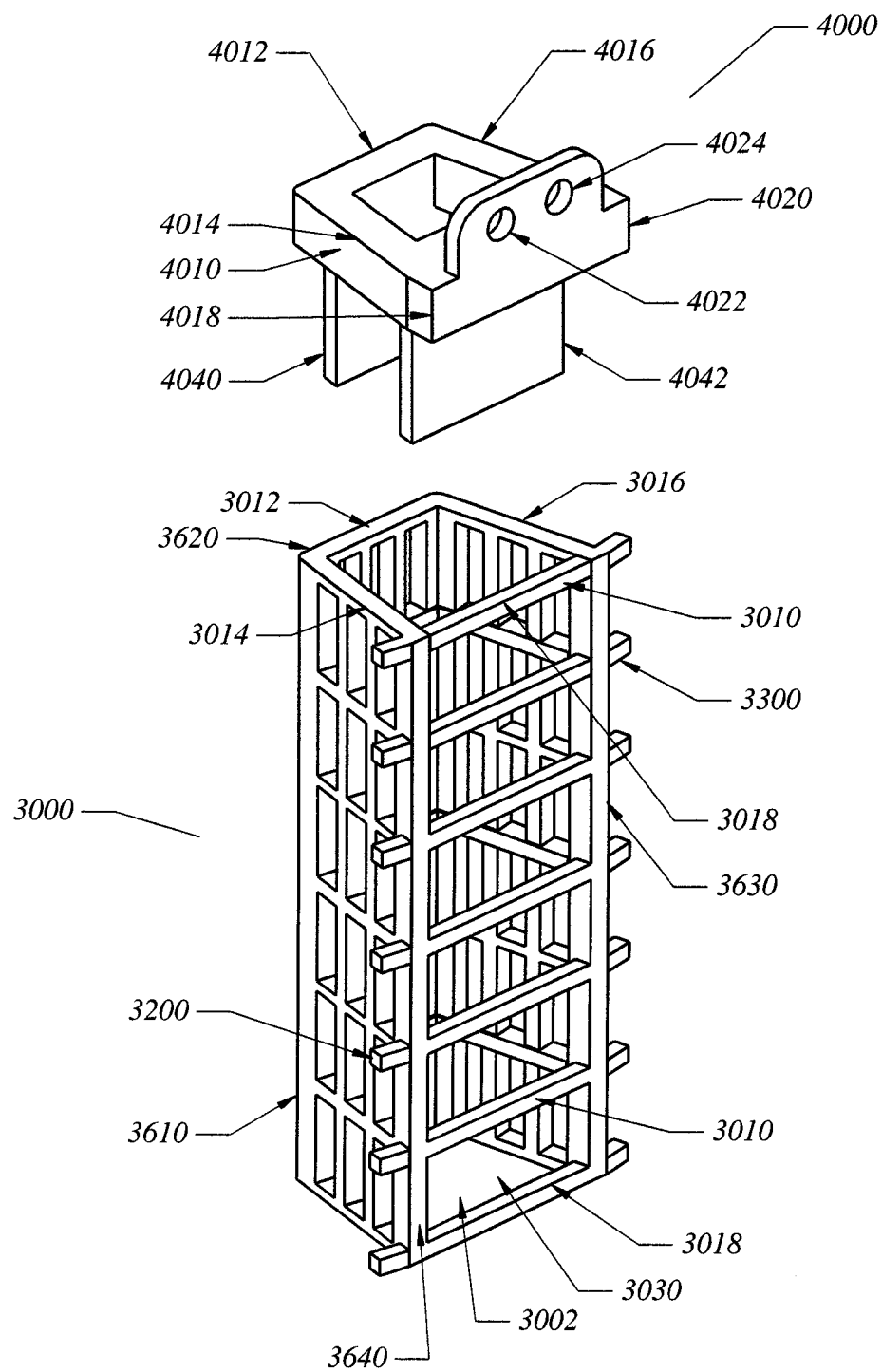
FIG. 1 is an exploded perspective enabling a biocompatible cage and end cap combination.

Although the disclosure hereof is detailed to enable those skilled in the art to practice the invention, the embodiments published herein merely exemplify the present invention.

In the most general sense, the present invention is a spinal implant that can be inserted into a cavity of the spinal column. Surgical removal of mammalian spinal tissue in one or more spinal regions creates the cavity or cavities that will receive the implant or implants. It has been discovered that many embodiments of the current implant can be useful for spine surgeries and can assist in stabilizing injured, deformed and or degenerative spines. Preferred embodiments of the current invention can be employed with cervical, thoracic or lumbar spinal procedures. Still other preferred embodiments of the present invention are particularly suited for corpectomy or partial corpectomy procedures.

After insertion of the implant into the cavity, the combination of a first spinal device, a second spinal device and the spacer assist in stabilizing the spinal column against rotational movement as well as resisting compression forces associated with gravity on the spinal column. It has been discovered that the current spacer and spinal implant is particularly useful for assisting in the restoration of normal anatomical height and angulation of an abnormal vertebral body. Select preferred embodiments of the present invention can be implanted through the patient's anterior or ventral side. The current spinal implants are custom fitted for the surgical cavity into which they will be inserted, e.g., a cage can be manufactured to fit the surgical cavity or a cage can be severed across a first cross section or a cage can be severed across first and second cross sections to size the cage to fit the cavity.

Some preferred embodiments of the current biocompatible cage and end cap can be generally trapezoidal in shape. Other preferred embodiments of the current can have generally square or rectangular dimensions. Preferred embodiments of the current spacer and spinal implants are manufactured of titanium alloys, stainless steel, resorbable polymers, non-resorbable polymers or any other composition acceptable in the art.

Within the scope of the present invention, it has advantageously been discovered that the trapezoidal cages can have a width of from about six to about fifteen millimeters, as measured along the narrowest parallel of the trapezoid, and a depth of from about eight millimeters to about fifteen millimeters, as measured along a converging side of the trapezoid. Generally the spacing between dividers of the cage is from about five to about ten millimeters, as measured from outward side to outward side of the series of dividers. Openings of the cages of the current invention into which bone graft, osteogenic and/or arthrodesis accelerating substances are packed can have areas from about 36 millimeters$^2$ to 225 millimeters$^2$ or greater. Custom made biocompatible cages can have lengths ranging from about twelve millimeters to about seventy millimeters.

Preferred embodiments of the end caps of the present invention have dimensions that are compatible with biocompatible cage. In select preferred embodiments, the slides can extend away from the body of the end cap for distances of from about two millimeters to about fifteen millimeters. Some preferred embodiments of the end caps can be provided with bores capable of engaging spikes that extend away from the biocompatible cage.

Preferred embodiments of the spacers of the current invention can have legs with heights ranging from three to about ten millimeters. Anterior widths of the spacers range from about six millimeters to about fifteen millimeters. The heights of anterior sections of the spacers can range of up to about seven millimeters. And depths of the spacers can range from about six millimeters to more than fifteen millimeters.

Meeting a long felt but unfilled need in the spinal surgical arts, the novel and unique structures of the present combinations allow the surgical team to, among other things, enhance the length of the spinal column from about two millimeters to about twenty millimeters more than the span of the biocompatible cage, when the patient's medical condition requires. Contact between the surgical cavity wall and a wedge-like cage preferred embodiment of the current invention can also inhibit the implant from contacting the spinal cord. Openings of the current spinal implant, in close proximity with the cavity's walls, increases the probability of the osteogenic materials and/or arthrodesis accelerating substances procuring a blood supply. And it is believed that increasing the blood supply to the osteogenic materials held by the cage enhances local areas of arthrodesis between the vertebra and the bone graft. Select preferred embodiments of the present invention are provided with lateral brakes to further impede the implant from contacting the spinal column.

FIG. 1 is an exploded perspective enabling a biocompatible cage (3000) and end cap (4000) combination. Biocompatible cage (3000) has a series of trapezoidal dividers or braces (3010) and a plurality of receptacles (3002) that can be packed with osteogenic materials, arthrodesis accelerating substances or other substances prior to the completion of spinal surgery. Cage (3000) is manufactured of titanium, stainless steel, resorbable polymers, non-resorbable polymers or combinations thereof. By way of illustration, dividers or braces (3010) have inward sides (3012) (after insertion into the surgically created cavity, positioned near the dura mater of the spinal cord), outward side (3018) (proximate the surgeon after insertion into the surgically created cavity), first converging or lateral side (3014) and second converging or lateral side (3016). The combination of each inward side (3012), outward side (3018), first converging side (3014) and second converging side (3016) creates trapezoidal aperture (3030). Select preferred embodiments of biocompatible cage (3000) can be provided with one or more lateral brakes (3200, 3300).

A preferred embodiment of end cap (4000) is provided with cage facing border or boundary (4010) proximate biocompatible cage (3000) and plate (4020). After insertion into the patient, outward sides of biocompatible cage (3000) and end cap (4000) are proximate the surgical team. In select preferred embodiments, border (4010) and plate (4020) are integral. Plate (4020) is provided with openings (4022, 4024) for receiving fasteners (not shown in this view). The fasteners, such as screws, are capable of securely attaching plate (4020) to bone. When the combination of cage (3000) and end cap (4000) are assembled as a unit, plate (4020) extends outward and away from border or boundary (4010) in a longitudinal direction parallel the lengthwise axis of biocompatible cage (3000). Boundary (4010) includes shortest side (4012), longest side (4018), first converging side (4014) and second converging side (4016). Extending from border (4010) toward cage (3000) are parallel docking slides (4040, 4042) for engaging inward side (3012) and outward side (3018) of outermost brace (3010) of cage (3000). As shown, docking slides (4040, 4042) are without surface areas adapted for impeding removal of the docking slides (4040, 4042) from biocompatible cage (3000). (As shown in FIG. 1, border (4010) is a four-side trapezoidal configuration. However, within the scope of the present invention, when engineering parameters require, other borders (4010) can be polygonal, squared or rectangular.

Figure 2:
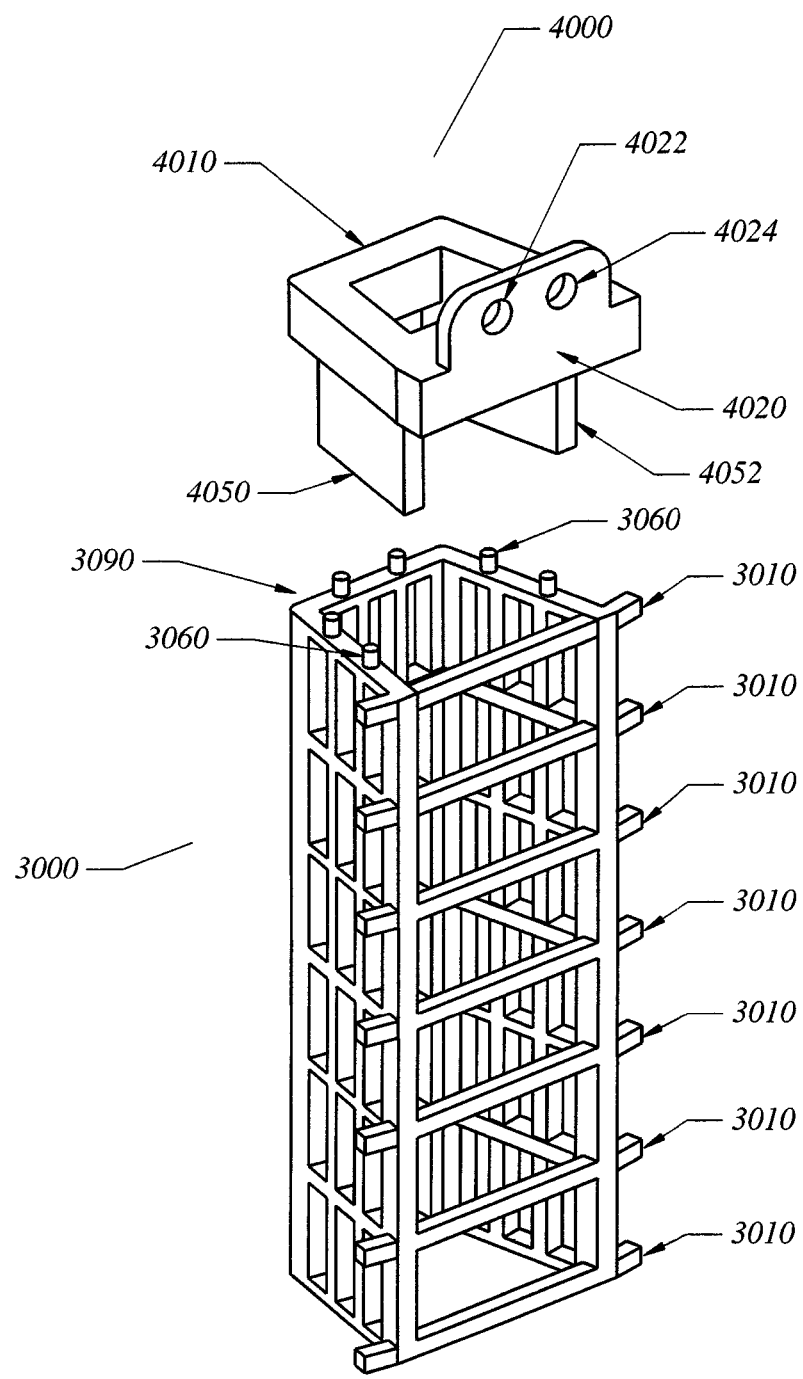
FIG. 2 is another preferred embodiment of the biocompatible cage utilizing spikes.

With reference to FIG. 2, another preferred embodiment of biocompatible cage (3000) utilizing spikes (3060) is enabled. Except for spikes (3060) and the docking slides (4050 and 4052), the structural elements for the FIG. 2 cage (3000) are identical to the structures enabled by FIG. 1. As shown in FIG. 2, docking slides (4050 and 4052) are not parallel the other. Instead, docking slide (4050) is parallel first converging side (4014) of border (4010) for engaging first converging side (3014) of outermost brace (3010) of cage (3000) and docking slide (4052) is parallel second converging side (4016) of border (4010) for engaging second converging side of outermost brace (3010) of cage (3000).

Figure 3:
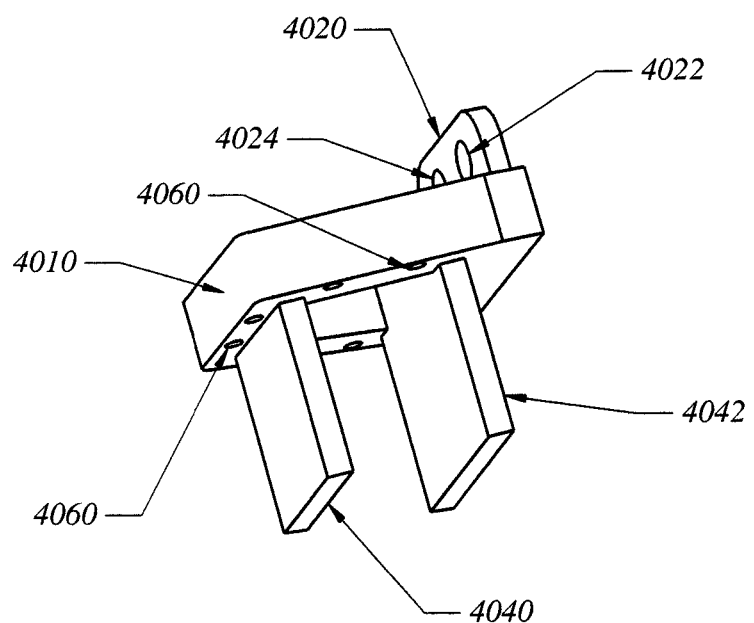
FIG. 3 is a perspective of a preferred embodiment of an implant facing side of a border of the end cap.

FIG. 3 is a perspective of a preferred embodiment of an implant facing side of border (4010) of end cap (4000). Along with docking slides (4040) and (4042), implant facing side of border (4010) is provided with bores (4060) capable of aligning with spikes (3060) of cage (3000). Other select preferred embodiments of end cap (4000) do not include bores (4060).

Figure 4:
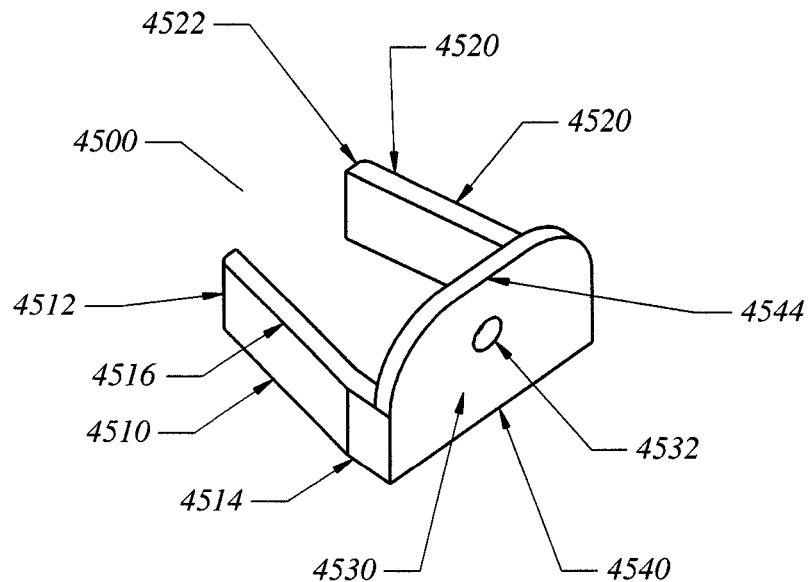
FIG. 4 is a perspective of a preferred embodiment of a spacer capable of being positioned between the cage or first spinal device and the end cap or second spinal device.
Figure 5:
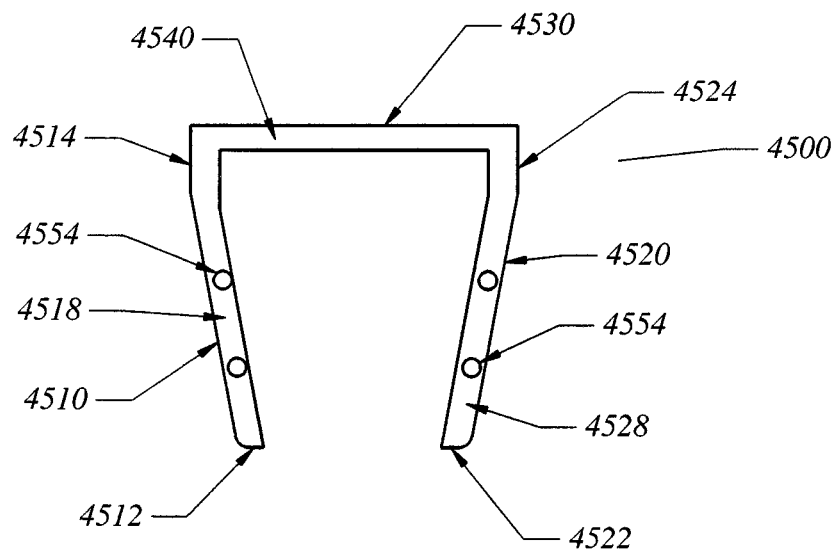
FIG. 5 is a plan view of a coplanar margin of the spacer.

FIG. 4 is a perspective of a preferred embodiment of a spacer (4500) capable of being positioned between cage or first spinal device (3000) and end cap or second spinal device (4000). Spacer (4500) has first leg (4510) and second leg (4520). As shown in FIGS. 4 and 5, distal end (4512) of first leg (4510) and distal end (4522) of second leg (4520) converge toward the other. In other words, as shown in FIG. 4, inward ends of the spacer's (4500) legs (4510, 4520) are closer than outward ends of legs (4510, 4520). However, within the scope of the present invention, when engineering parameters require, first and second legs (4510 and 4520) can be parallel the other or diverging from the other.

With reference to FIG. 4, anterior section (4530) of spacer (4500) joins a first or outward end (4514) of first leg (4510) and a second or outward end (not shown in FIG. 4) of second leg (4520). Anterior section (4530), first leg (4510) and second leg (4520) share a coplanar margin (4540) that faces cage (3000). Anterior section (4530) is provided with a second margin (4544) opposite coplanar margin (4540) that extends in a longitudinal direction further away from biocompatible cage (3000). In select preferred embodiments of extension (4000), anterior section (4530) includes hole (4532) capable of being engaged by a surgical tool (not shown in this view).

FIG. 5 is a plan view of coplanar margin (4540) of spacer (4500). For select preferred embodiments of the current invention, second side (4518) of first leg (4510) and second side (4528) of second leg (4520) are provided with apertures (4554) capable of receiving spikes (3060) of biocompatible cage (3000). In other select preferred embodiments of spacer (4500), first and second legs (4520, 4520) are not provided with apertures.

Figure 6:
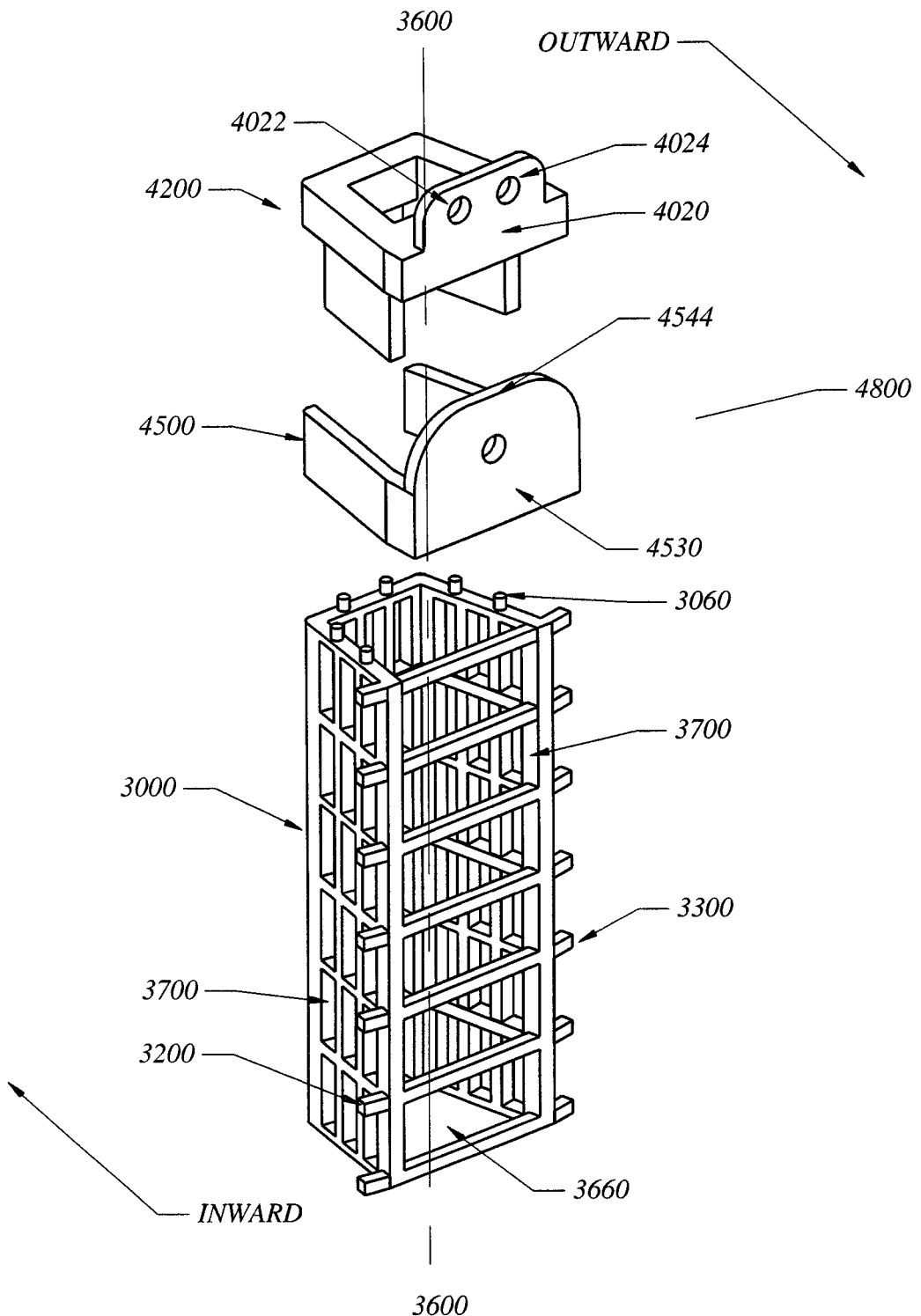
FIG. 6 is an exploded perspective showing a preferred embodiment of the combination of the biocompatible cage, spacer and end cap.
Figure 7:
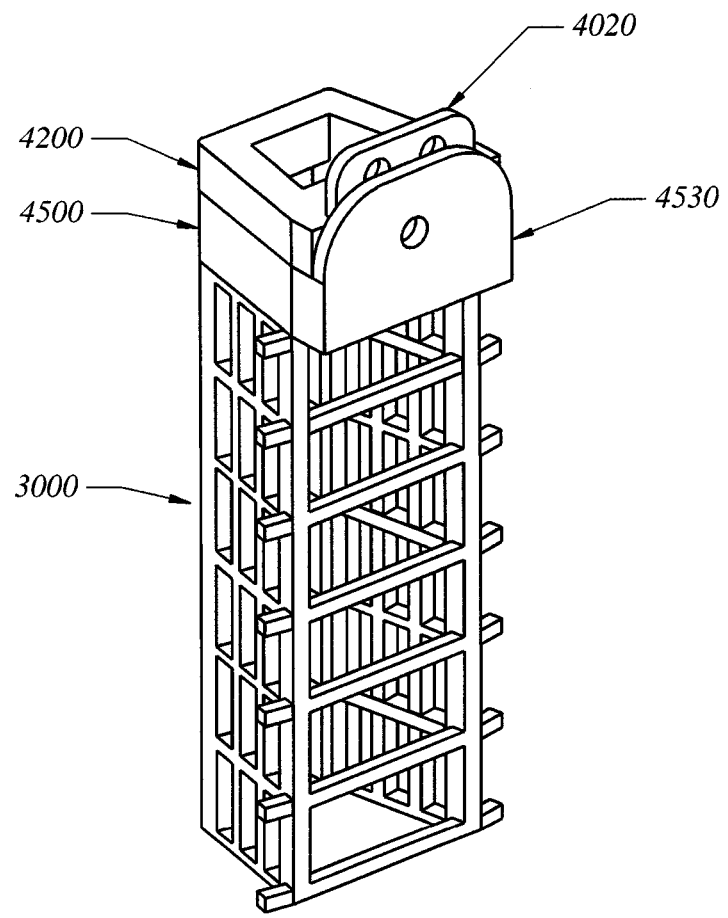
FIG. 7 is a perspective showing a preferred embodiment of the in-use combination that includes the combination of the biocompatible cage, spacer and end cap.

FIG. 6 is an exploded perspective showing a preferred embodiment of the combination (4800) of biocompatible cage (3000), spacer (4500) and end cap (4200). FIG. 7 is a perspective showing a preferred embodiment of the in-use combination (4800) that includes biocompatible cage (3000), spacer (4500) and end cap (4200). In the practice of the current spinal implant (4800), spacer (4500) is sandwiched or positioned between the combination's (4800) first spinal device and the second spinal device.

As shown in FIGS. 6 and 7, when biocompatible cage (3000), spacer (4500) and end cap (4200) (previously described and also shown in FIGS. 1-3) are fully engaged within the surgical cavity, anterior section (4530) of spacer (4500) is anterior to plate (4020) of end cap (4200). Second margin (4544) and anterior section (4530) of spacer (4500) sufficiently cover openings (4022 and 4024) to prevent fasteners (not shown in this view) from backing out of plate (4020) of end cap (4200).

With reference to FIGS. 1 and 6, sides (3610, 3620, 3630, 3640) surround a central or a common longitudinal axis (3600) of biocompatible cage (3000) where the central or common longitudinal axis (3600) extends through the length of biocompatible cage (3000), spacer (4500) and end cap (4200). Sides (3610, 3620, 3630, 3640) of biocompatible cage (3000) create channel (3660) and are also provided with one or more openings (3700) capable of exposing osteogenic substances to a surgically created cavity. For select preferred embodiments, the inward side of biocompatible cage (3000) is of lesser width than the opposed outward side of biocompatible cage (3000). And preferred embodiments of biocompatible cage (3000) can be provided with brakes (3200, 3300) extending laterally from the face of biocompatible cage (3000).

As shown in FIG. 6, biocompatible cage (3000) of spinal implant (4800) is provided with spikes (3060). However in other preferred embodiments of the current spinal implant (4800), similar to biocompatible cage (3000) of FIG. 1, biocompatible cage (3000) is not provided with spikes.

Figure 8:
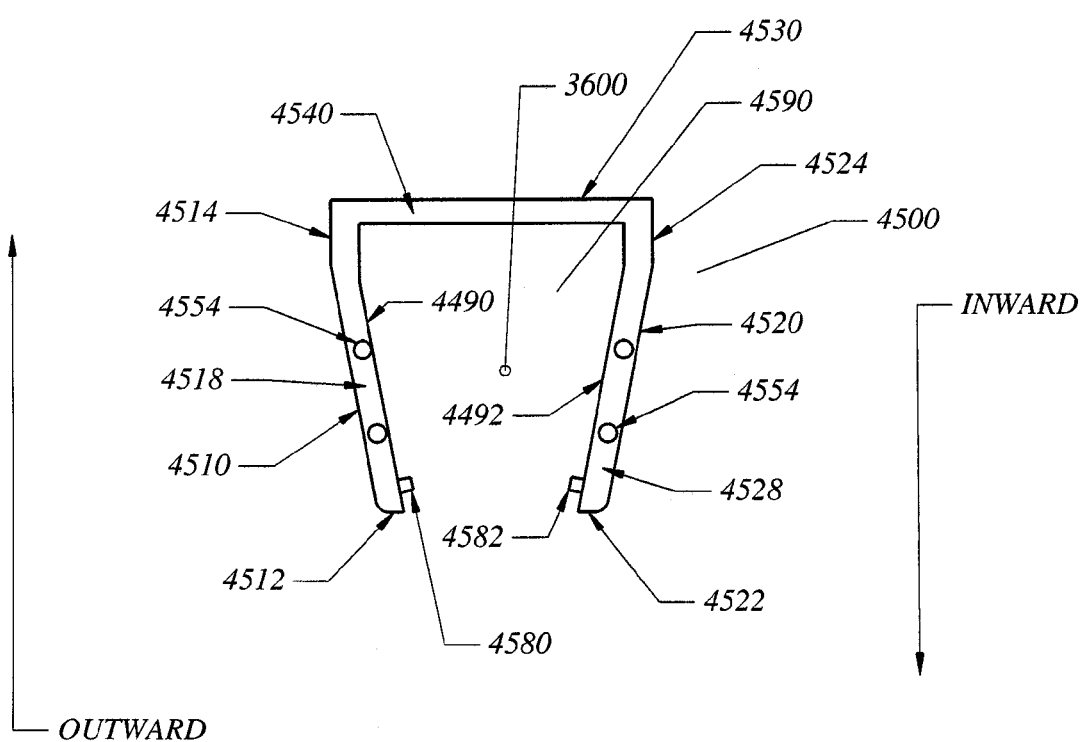
FIG. 8 is a frontal view of the cage-facing side of a preferred embodiment of spacer.

FIG. 8 is a view of the cage-facing side of a preferred embodiment of spacer (4500). Second side (4518) of first leg (4510) of spacer (4500) and second side (4528) of second leg (4520) of spacer (4500) are provided with apertures (4554) capable of receiving spikes (3060) of biocompatible cage (3000). Other preferred embodiments of spacer (4500) are not provided with apertures. Anterior section (4530) of spacer (4500) joins a first or outward end (4514) of first leg (4510) and a second or outward end (4524) of second leg (4520). Anterior section (4530), first leg (4510) and second leg (4520) can share a coplanar margin (4540) that faces cage (3000). As shown in the FIG. 8 preferred embodiment, a first ridge (4580) is positioned on the central longitudinal axis facing side (4490) of first leg (4510) and a second ridge (4582) is positioned on the central longitudinal axis facing side (4492) of second leg (4520). The arrangement of first ridge (4580), second ridge (4582) and margin (4540) of spinal implant (4500) create catch (4590) capable of engaging docking slides (4040, 4042) of end cap (4200). Within the scope of the present invention, other preferred embodiments of spacer (4500) do not include ridges (4580, 4582).

Having disclosed the invention as required by Title 35 of the United States Code, Applicant now prays respectfully that Letters Patent be granted for his invention in accordance with the scope of the claims appended hereto.

What is claimed is:

1. A spinal implant configured to be inserted about a surgically created cavity proximate to one or more vertebrae; said spinal implant comprising:
   a) a biocompatible cage comprising:
      i) a length having a central longitudinal axis and a plurality of sides, wherein at least some of said sides comprise a plurality of openings surrounding a channel; said openings capable of exposing osteogenic or arthrodesis accelerating substances to said surgically created cavity; and
      ii) a first end perimeter comprising an open entry into said channel;
   b) an end cap comprising:
      i) a border facing said biocompatible cage;
      ii) a plate extending in a lengthwise direction, parallel said central longitudinal axis, away from said border and comprising at least one opening capable of receiving a fastener; and
      iii) a pair of opposed docking slides extending from said border toward said biocompatible cage; said docking slides adapted to engage inward sides of said biocompatible cage; and
   c) a spacer adapted for allowing adjustment of length of said spinal implant and sandwiched between said biocompatible cage and said end cap; said spacer comprising:
      i) a first leg extending toward the inward side of said spinal implant;
      ii) a second leg opposed from said first leg and extending toward the inward of said spinal implant;
      iii) a first ridge positioned on said central longitudinal axis facing side of said first leg and a corresponding second ridge positioned on an said central longitudinal axis facing side of said second leg; and
      iv) an anterior section anterior to said plate; said anterior section sharing a margin with outward ends of said first and said second legs and extending in a lengthwise direction parallel said central longitudinal axis, wherein said docking slides engage a catch created by an arrangement of said first ridge, said second ridge and said margin.

2. The spinal implant of claim 1, wherein said central longitudinal axis extends through an orifice of said end cap.

3. The spinal implant of claim 2 comprising brakes extending laterally from an anterior face of said cage.

4. The spinal implant of claim 3, wherein:
   a) inward ends of said first leg and said second leg are closer to each other than outward ends of said first leg and said second leg; and
   b) an inward side of said cage is of lesser width than an opposed outward side of said cage.

5. A spinal implant configured to be inserted about a surgically created cavity proximate to one or more vertebrae; said spinal implant comprising:
   a) a biocompatible cage comprising:
      i) a length having a central longitudinal axis and a plurality of sides, wherein at least some of said sides comprise a plurality of openings surrounding a channel; said openings capable of exposing osteogenic or arthrodesis accelerating substances to said surgically created cavity; and
      ii) a first end perimeter comprising an open entry into said channel;
   b) an end cap comprising:
      i) a border facing said biocompatible cage;
      ii) a plate extending in a lengthwise direction, parallel said central longitudinal axis, away from said border and comprising at least one opening capable of receiving a fastener; and
      iii) a pair of opposed docking slides extending from said border toward said biocompatible cage; said docking slides adapted to engage inward sides of said biocompatible cage, wherein said docking slides' surfaces engaging said inward sides of said biocompatible cage are without surface areas adapted for impeding removal of said docking slides from said biocompatible cage; and
   c) a spacer adapted for allowing adjustment of length of said spinal implant and sandwiched between said biocompatible cage and said end cap; said spacer comprising:
      i) a first leg extending toward the inward side of said spinal implant;
      ii) a second leg opposed from said first leg and extending toward the inward side of said spinal implant; and
      iii) an anterior section anterior to said plate; said anterior section sharing a margin with outward ends of said first and said second legs and extending in a lengthwise direction parallel said central longitudinal axis.

6. The spinal implant of claim 5, wherein said central longitudinal axis extends through an orifice of said end cap.

7. The spinal implant of claim 6, wherein:
   a) a first ridge is positioned on said central longitudinal axis facing side of said first leg and a corresponding second ridge is positioned on said central longitudinal axis facing side of said second leg.

8. The spinal implant of claim 7 comprising brakes extending laterally from an anterior face of said cage.

9. The spinal implant of claim 8, wherein said docking slides engage a catch created by an arrangement of said first ridge, said second ridge and said margin.

10. The spinal implant of claim 9, wherein:
    a) inward ends of said first leg and said second leg are closer to each other than outward ends of said first leg and said second leg; and b) an inward side of said cage is of lesser width than an opposed outward side of said cage.

* * * * *